United States Patent [19]

Ensminger et al.

[11] Patent Number: 5,607,393
[45] Date of Patent: Mar. 4, 1997

[54] IMPLANTABLE ACCESS DEVICES

[75] Inventors: William D. Ensminger; Robert F. Gavin, both of Ann Arbor, Mich.

[73] Assignee: Michigan TransTech Corporation, Ann Arbor, Mich.

[21] Appl. No.: 490,605

[22] Filed: Jun. 6, 1995

Related U.S. Application Data

[63] Continuation of Ser. No. 442,722, May 15, 1995, Pat. No. 5,554,117, which is a continuation-in-part of Ser. No. 259,053, Jun. 13, 1994, Pat. No. 5,417,656, which is a continuation of Ser. No. 148,394, Nov. 8, 1993, Pat. No. 5,350,360, which is a division of Ser. No. 940,619, Sep. 4, 1992, Pat. No. 5,281,199, which is a continuation-in-part of Ser. No. 818,626, Jan. 10, 1992, Pat. No. 5,226,879, which is a continuation-in-part of Ser. No. 654,661, Feb. 15, 1991, Pat. No. 5,180,365, which is a continuation-in-part of Ser. No. 539,793, Jun. 18, 1990, Pat. No. 5,053,013, which is a continuation-in-part of Ser. No. 487,541, Mar. 1, 1990, Pat. No. 5,057,084.

[51] Int. Cl.⁶ ................................................ A61M 5/00
[52] U.S. Cl. ...................................... 604/93; 604/175
[58] Field of Search ............................. 604/93, 86, 83, 604/82, 280, 283, 243, 242, 167, 175

[56] References Cited

U.S. PATENT DOCUMENTS

| | | |
|---|---|---|
| 3,288,137 | 1/1964 | Lund . |
| 3,402,710 | 9/1968 | Paleschuck . |
| 3,565,078 | 2/1971 | Vaillancourt et al. . |
| 3,699,956 | 10/1972 | Kitrilakis . |
| 4,181,132 | 1/1980 | Parks . |
| 4,190,040 | 2/1980 | Schulte . |
| 4,230,109 | 10/1980 | Geiss . |
| 4,256,102 | 3/1981 | Monaco . |
| 4,314,568 | 2/1982 | Loving . |
| 4,387,879 | 6/1983 | Tauschinski . |
| 4,405,320 | 9/1983 | Cracauer et al. . |
| 4,425,119 | 1/1984 | Berglund . |
| 4,430,081 | 2/1984 | Timmermans . |
| 4,439,188 | 3/1984 | Dennehey et al. . |
| 4,447,237 | 5/1984 | Frisch et al. . |
| 4,464,178 | 10/1984 | Dalton . |
| 4,490,137 | 12/1984 | Moukheibir . |
| 4,491,126 | 1/1985 | Cullor . |
| 4,534,759 | 8/1985 | Trawöger . |
| 4,543,088 | 9/1985 | Bootman et al. . |
| 4,547,194 | 10/1985 | Moorehead . |
| 4,569,675 | 2/1986 | Prosl et al. . |

(List continued on next page.)

FOREIGN PATENT DOCUMENTS

| | | |
|---|---|---|
| 0119596 | 3/1984 | European Pat. Off. . |
| 134745 | 8/1984 | European Pat. Off. . |
| 0132940A1 | 7/1985 | European Pat. Off. . |
| 1296652 | 5/1962 | France . |
| 3242870 | 6/1983 | Germany . |
| 3528878 | 2/1987 | Germany . |
| 2192338 | 1/1988 | United Kingdom . |
| 8300367 | 2/1983 | WIPO . |

*Primary Examiner*—John D. Yasko
*Attorney, Agent, or Firm*—Harness, Dickey & Pierce, PLC

[57] ABSTRACT

An implantable access device which permits the introduction of an external filament such as a catheter, guide wire or optical fiber into a patient for communication with an internal catheter located within the body of the patient. The device includes a housing having inlet and outlet openings and a passageway communicating between the openings. The first sealing mechanism provides resistance to fluid flow through the passageway when the external filament is not present within the device. This first sealing mechanism allows the transfer of fluids through the passageway when the filament is present within the passageway. A second sealing mechanism engages and seals about the exterior perimeter of the external filament when the filament is located within the device.

18 Claims, 4 Drawing Sheets

U.S. PATENT DOCUMENTS

| | | |
|---|---|---|
| 4,578,061 | 3/1986 | Lemelson . |
| 4,578,063 | 3/1986 | Inmann et al. . |
| 4,581,020 | 4/1986 | Mittlemab . |
| 4,623,329 | 11/1986 | Drobish et al. . |
| 4,634,422 | 1/1987 | Kantrowitz et al. . |
| 4,645,495 | 2/1987 | Vaillancourt . |
| 4,650,473 | 3/1987 | Bartholomew et al. . |
| 4,673,394 | 6/1987 | Fenton, Jr. et al. . |
| 4,682,981 | 7/1987 | Suzuki et al. . |
| 4,692,146 | 9/1987 | Hilger . |
| 4,695,273 | 9/1987 | Brown . |
| 4,704,103 | 11/1987 | Stober et al. . |
| 4,710,167 | 12/1987 | Lazorthes . |
| 4,710,174 | 12/1987 | Moden et al. . |
| 4,712,583 | 12/1987 | Pelmulder et al. . |
| 4,781,680 | 11/1988 | Redmond et al. . |
| 4,781,693 | 11/1988 | Martinez et al. . |
| 4,781,695 | 11/1988 | Dalton . |
| 4,790,826 | 12/1988 | Elftman . |
| 4,810,241 | 3/1989 | Rogers . |
| 4,832,054 | 5/1989 | Bark . |
| 4,842,591 | 6/1989 | Luther . |
| 4,857,053 | 8/1989 | Dalton . |
| 4,857,062 | 8/1989 | Russell . |
| 4,886,501 | 12/1989 | Johnston et al. . |
| 4,915,690 | 4/1990 | Cone et al. . |
| 4,929,235 | 5/1990 | Merry et al. . |
| 4,978,338 | 12/1990 | Melsky . |
| 5,026,344 | 6/1991 | Dijkstra et al. . |
| 5,041,098 | 8/1991 | Loiterman et al. . |
| 5,045,060 | 9/1991 | Melsky et al. . |
| 5,053,013 | 10/1991 | Ensminger et al. . |
| 5,057,084 | 10/1991 | Ensminger et al. . |
| 5,092,849 | 3/1992 | Sampson . |
| 5,171,228 | 12/1992 | McDonald . |
| 5,180,365 | 1/1993 | Ensminger et al. . |
| 5,226,879 | 7/1993 | Ensminger et al. . |
| 5,263,930 | 11/1993 | Ensminger et al. . |
| 5,281,199 | 1/1994 | Ensminger et al. . |
| 5,318,545 | 6/1994 | Tucker . |
| 5,350,360 | 9/1994 | Ensminger et al. . |
| 5,352,204 | 10/1994 | Ensminger . |
| 5,356,381 | 10/1994 | Ensminger et al. . |
| 5,395,324 | 3/1995 | Hinrichs et al. . |
| 5,417,656 | 5/1995 | Ensminger et al. . |

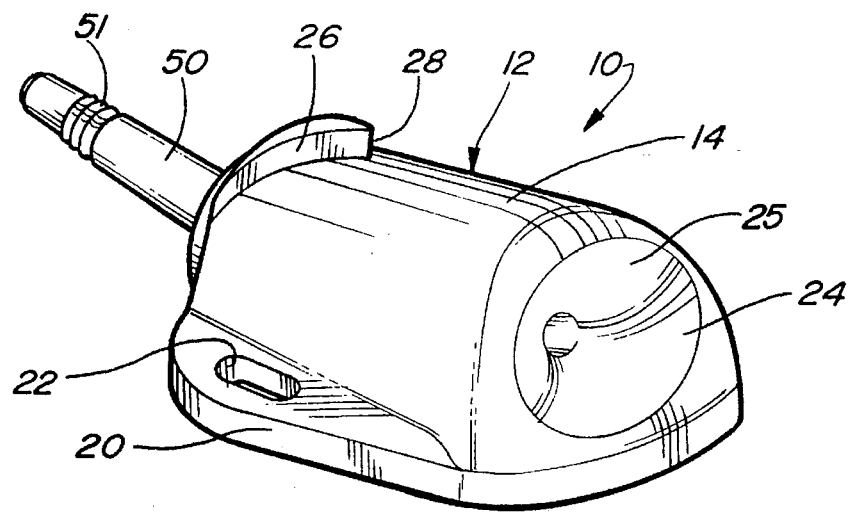
Fig-1
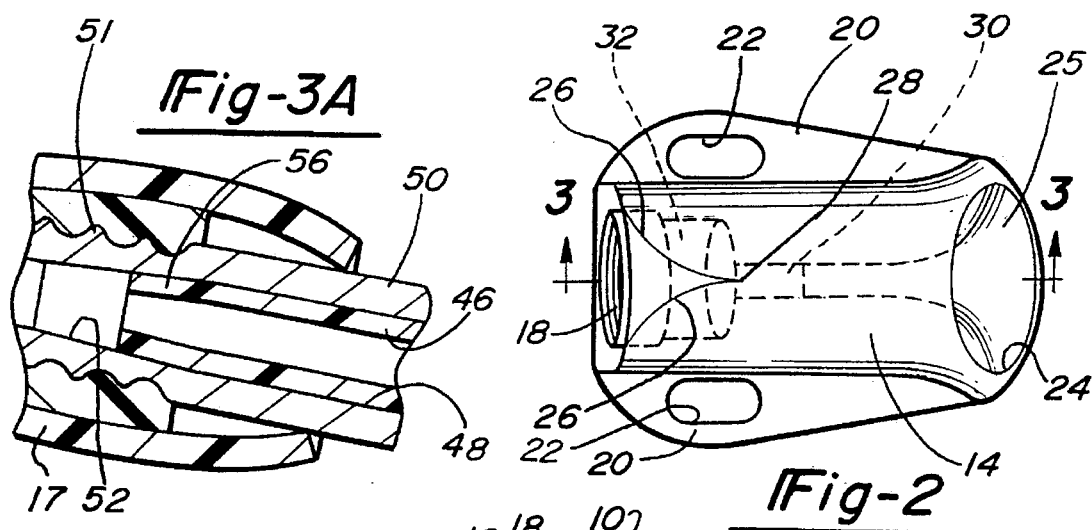
Fig-3A
Fig-2
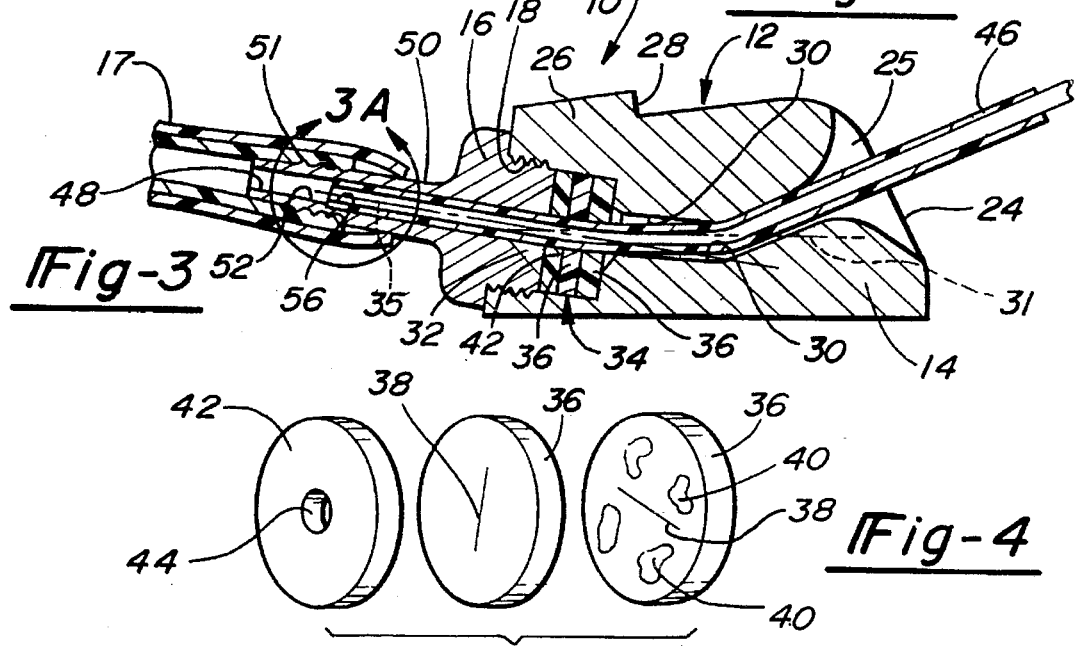
Fig-3
Fig-4

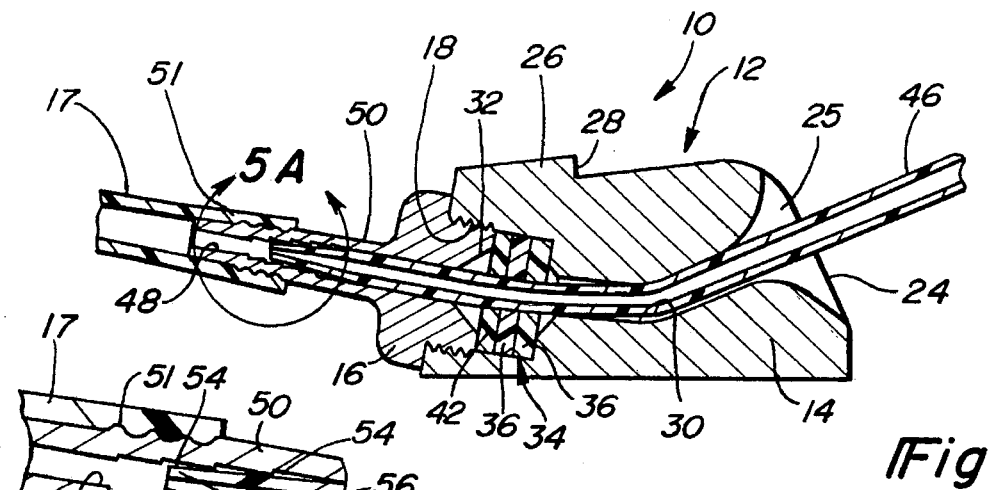
Fig-5
Fig-5A
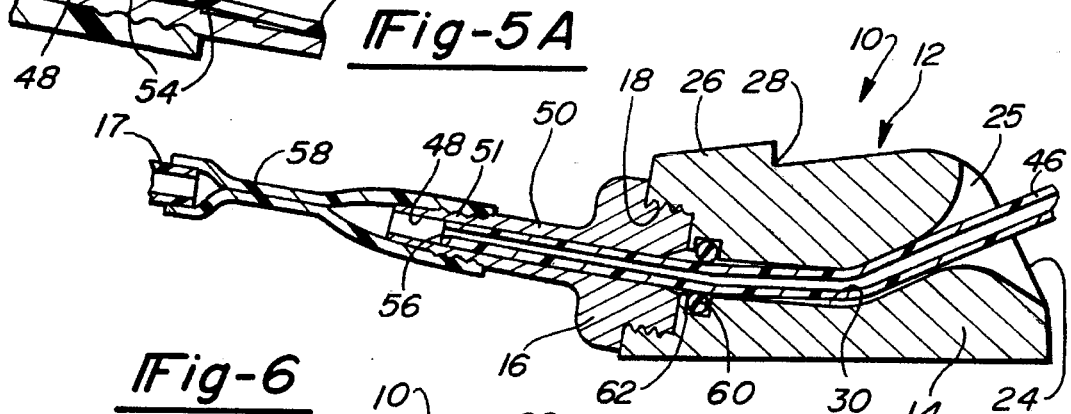
Fig-6
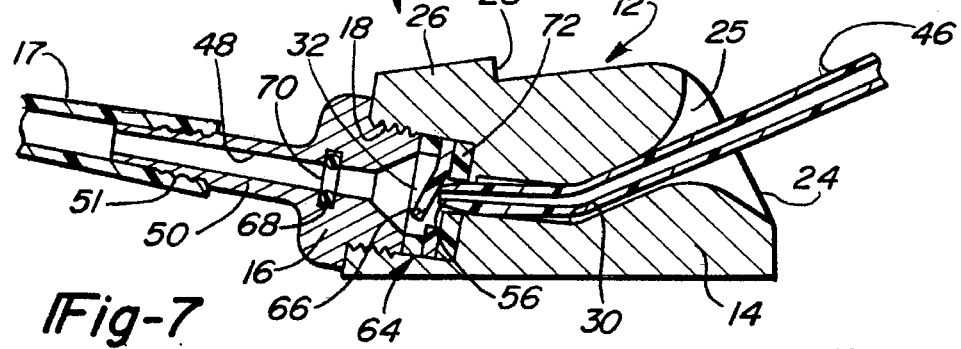
Fig-7
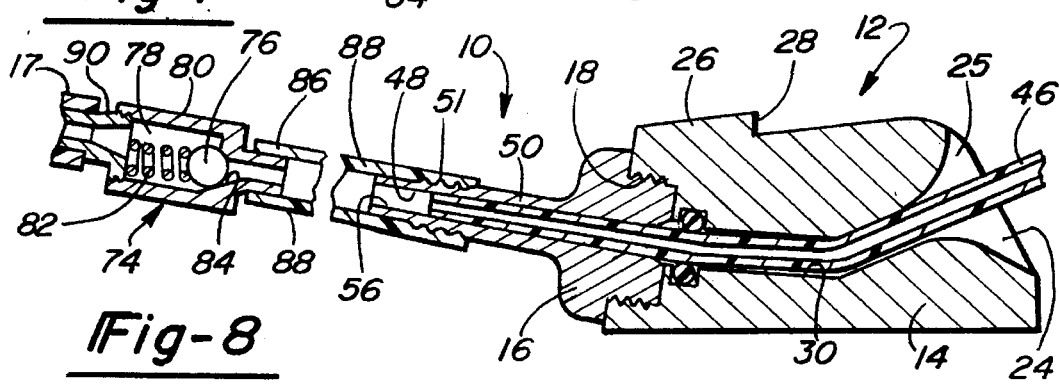
Fig-8

IMPLANTABLE ACCESS DEVICES

CROSS-REFERENCE TO RELATED APPLICATIONS

This application is a continuation of U.S. patent application Ser. No. 08/442,722, filed May 15, 1995, Attorney Docket No. 7882-00001/CPN now U.S. Pat. No. 5,554,117, which is a continuation-in-part of U.S. application Ser. No. 259,053, filed Jun. 13, 1994, now U.S. Pat. No. 5,417,656, which is a continuation of U.S. application Ser. No. 148,394, filed Nov. 8, 1993 (now U.S. Pat. No. 5,350,360), which is a divisional of U.S. application Ser. No. 940,619, filed Sep. 4, 1992 (now U.S. Pat. No. 5,281,199), which is a continuation-in-part of U.S. application Ser. No. 818,626 filed Jan. 10, 1992 (now U.S. Pat. No. 5,226,879), which is a continuation-in-part of U.S. application Ser. No. 654,661 filed Feb. 15, 1991 (now U.S. Pat. No. 5,180,365), which is a continuation-in-part of U.S. application Ser. No 539,793 filed Jun. 18, 1990 (now U.S. Pat. No. 5,053,013), which is a continuation-in-part of U.S. application Ser. No. 487,541 filed Mar. 1, 1990 (now U.S. Pat. No. 5,057,084); the disclosures of which are hereby incorporated by reference and are collectively referred to as "related applications" herein.

FIELD OF THE INVENTION

This invention relates to devices permitting the introduction of an external filament, such as a catheter, into a patient for infusing a therapeutic or diagnostic agent to a desired site or withdrawing fluid from the patient or for permitting access by other filaments such as a guide wire, fiber optic sensor etc. to a desired site within the body of a patient. The device thus enables the filament to communicate either directly or indirectly, with or without physical contact, with a desired site within the body of the patient. More particularly, the invention relates to devices which are completely implanted within the body of the patient. While completely implanted, the present invention is designed so as to facilitate repeated access by the percutaneous route.

BACKGROUND AND SUMMARY OF THE INVENTION

In current human and animal medical practice, there are numerous instances where therapeutic or diagnostic agents must be delivered to a specific organ or tissue within the body. One example is the lengthy treatment period where chemotherapy is infused into a central vein on a recurring basis in an attempt to treat widespread sites of malignant tumors. Without a device for intravenous drug infusion, multiple vein punctures over a lengthy period of time would result in progressive thrombosis, venous sclerosis, and destruction of small diameter peripheral vessels. In other situations, it may be desirable to infuse chemotherapy to a localized malignant tumor site. Delivering an agent specifically to such a site on a regular repetitive basis without surgically implanting an infusion system would prove difficult if not impossible. Similarly, repeated arterial access is occasionally needed to inject an X-ray dye or contrast agent into an artery for diagnostic purposes. In still other situations, there is a need to repetitively remove a body fluid from a remote body site for analysis. Finally, sensing and physiological measuring devices incorporated into small diameter catheters and optical fibers are increasingly being utilized for monitoring body processes and could be more easily implemented through a properly designed access device with an adequate internal diameter.

In prior medical practice, percutaneous catheters have been used to provide vascular or organ access for drug therapy or the withdrawal of body fluids. Although such systems generally performed in a satisfactory manner, numerous problems were presented by such therapy approaches. These problems included, without limitation the substantial care requirements of the patients, e.g. dressing changes with sterile techniques, a significant rate of infection of the catheter because of its transcutaneous position, and a high rate of venous thrombosis, particularly if the catheter was located within an extremity vein.

Implantable infusion devices or "ports" have recently become available and represent a significant advance over transcutaneous catheters. Presently available infusion ports have a number of common fundamental design features. The ports themselves comprise a housing which forms a reservoir that can be constructed from a variety of plastic or metal materials. A surface of the reservoir is enclosed by a high-density, self-sealing septum, typically made of silicone rubber. Connected to the port housing is an implanted catheter which communicates with a vein or other site within the patient where the infusion of therapeutic agents is desired. Implantation of such devices generally proceeds by making a small subcutaneous pocket in an appropriate area of the patient under local anesthesia. The implanted catheter is tunnelled to the desired infusion site. When the physician desires to infuse or remove materials through the port, a hypodermic needle, which pierces the skin over the infusion port, is used and placed into the port.

Although the presently available implantable infusion ports generally operate in a satisfactory manner, they have a number of shortcomings. Since these devices rely on a compressed rubber septum for sealing and since large diameter needles can seriously damage the septum, there are limitations in the diameter of needles which can be used to penetrate the septum. These diameter limitations severely restrict the opportunities provided by the port. In cases where it is desirable to infuse drugs using a flexible external catheter, the catheter must be fed through the needle that penetrates the septum. Such catheters have an extremely small inside diameter and, therefore, impose severe limitations on both the fluid flow rate and limit the types of fibers which can be introduced.

During prolonged infusions using a conventional port, the infusion needle is taped to the patient's skin to hold it in position. Conventional ports do not allow the needle to penetrate deeply into the port. Because of this, a small displacement of the needle can cause the needle to be pulled from the port. In cases where locally toxic materials are being infused, extravasation of such materials can cause local tissue damage which itself may require corrective surgery such as skin grafting or removal of the damaged tissue.

Presently available implantable drug infusion devices also require a significant size in order to provide an acceptable target surface area for the physician who must locate the port and penetrate the septum with a needle. Since structure is required to maintain the septum in compression and provide for self-sealing after the needle is removed, the port housing becomes bulky as the septum size increases. Moreover, presently available infusion ports are difficult to clear if thrombosis occurs within the port or within the implanted catheter. This is difficult, if not impossible, because of the relative sizes of a cleaning wire which would have to be fed through the penetrating hypodermic needle in order to clear the infusion device and the internal catheter.

Present infusion ports also have a retained volume beneath the self-sealing septum. The retained volume increases the volume of drug which must be administered to enable a desired quantity to reach the infusion site. This retained volume also poses problems when a physician desires to successively deliver multiple drugs to the same infusion site, particularly when the drugs are incompatible when mixed. Additionally, when it is desired to withdraw blood through the port, the retained volume of the prior art infusion ports comprises an area where blood clotting can occur. This in turn can interfere with future access to the site. And finally, in present infusion ports, there is a risk that the physician attempting to pierce the port septum will not properly enter it, leading to the possibility of extravasation, which can cause significant undesirable consequences as mentioned above, or piercing of the implanted catheter itself.

The present invention relates to a family of implantable access ports which provide numerous enhancements over prior art devices. In accordance with this invention, an access port is provided which incorporates the funnel-shaped entrance orifice which narrows down to a reduced diameter guide passageway. The guide passageway terminates at an internal cavity which retains a catheter valve which may be an articulating type, such as a multi-element leaflet valve assembly. The port also has an exit passageway which is connected to an implanted catheter. This specification describes numerous embodiments of alternative designs of patient access ports of the type described in the related applications.

In prior embodiments of the present invention, various valving systems were described and claimed, including leaflet valves, ball valves, "flapper" type valves, etc. Each of these valve configurations is broadly encompassed by the description "articulating catheter valve" or "articulating valve"; meaning that one or more valve elements are displaced in some predictable manner to provide access and seal around the inserted filament and to return to an original position to provide a fluid seal against backflow through the valve assembly.

In order to operate successfully, the valve mechanism of the access port must perform two distinct functions. When the valve is not being used for access, the flow of fluids in either direction through the access port is to be avoided (i.e. "normal condition sealing"). When an external catheter is placed into the port, there is a need to seal around the outer diameter of the catheter to prevent fluid from flowing out of the entrance of the access port instead of through the port exit and into the implanted catheter (i.e. "use condition sealing"). In the related applications, these two distinct sealing functions were satisfied by a single valve assembly, which as mentioned before, could be a multiple element leaflet valve assembly.

In the present invention, valve configurations are described in which features providing normal condition sealing of the access port are separated from the features which provide use condition sealing. This alternative configuration is provided in several different specific embodiments. One such embodiment utilizes a check valve in the form of an elongated tube connected to the port and having an internal passageway that is normally maintained in a flattened, occluded condition when the fluid pressure within the passageway is the same as or less than the pressure acting upon the exterior of the valve. This valve provides normal or non-use condition sealing of the passageway. An implanted internal catheter is attached to this valve and an O-ring may be located within the access device to provide an additional seal around the perimeter of an inserted filament during actual use of the device. When the external catheter has been inserted into the access device, and a fluid is being infused, the pressure within the occluded conduit is increased to the point where the passageway inflates and the fluid is delivered to the desired tissue site through the internal catheter. Other types of fluid pressure actuated valves, as further discussed below, could alternatively be used.

In another embodiment, the O-ring or perimeter sealing member may be provided downstream (or upstream) of the valve which prevents backflow through the access port in the normal condition. As used herein, the terms upstream and downstream shall be determined relative to the source for the accessing catheter.

Upon insertion of a filament through the port, the valve is opened and the filament is inserted until circumferentially engaged by the O-ring. Once such embodiment could include insertion of the accessing catheter through the collapsed tube-type of valve described above.

In yet another embodiment similar to the first described above, a ball-type check valve is utilized which provides normal condition sealing.

In another aspect of the present invention, a novel mechanism is provided to limit the extent to which a flexible filament above a predetermined diameter, such as a twenty (20) gage ANGIOCATH™, can be inserted through the access port. In prior embodiments of this invention, as described in the related applications, mechanisms were provided where the insertion distance of a rigid filament, such as a hypodermic needle, is limited by features designed for that purpose. One needle stop approach is to provide a bend or redirection in a passageway either before of beyond the valve assembly. The bend is such that the inserted needle would be unable to engage the valve assembly due to its rigidity. A flexible filament, however, is capable of maneuvering a bend in the passageway and as such can be inserted completely through the access port and into the implanted catheter which communicates with the desired site in the patient. There may be instances where it is desirable to provide a means of limiting the depth of insertion of a flexible filament. In some applications, engagement of the flexible filament with the internal catheter can potentially lead to dislodging of the internal catheter from the discharge fitting of the access port or repositioning it. Moreover, some implanted catheters may not have an internal diameter sufficient to accommodate the external filament.

According to the present invention, a positive stop feature is provided whereby an internal flexible filament above a predetermined size is prevented from completely passing through the access port or implanted catheter. Accordingly, the catheter stop can be utilized to form the use condition seal of the access device. Slightly, smaller diameter filaments form a seal with the internal diameter of the passageway while still being movable through the entire access port and implanted catheter. In one embodiment, the internal diameter of the passageway through the discharge fitting of the access port is convergently tapered to a diameter which is less than the external diameter of the inserted filament. During insertion, the person inserting the flexible filament will be able to feel positive engagement of the filament with the stop as further insertion is prevented. This positive stop could also be achieved by progressively decreasing the diameter of the passageway through the discharge fitting in a series of stepped reduced diameter portions. Such a progressively stepped passageway could in turn be used as a stop for certain diameter catheters. Since engagement with the positive stop feature creates a seal around the outside of the external catheter, these features can be implemented to provide use condition sealing for multiple sizes of accessing catheter, either by themselves or in conjunction with "O-rings" provided elsewhere in the port.

In accordance with another aspect of the present invention, an access port is disclosed where the implanted catheter is shielded from being inadvertently engaged by a sharp instrument such as a needle or trocar being used to access the port. Such engagement might result where the person inserting the needle or trocar completely misses the entrance orifice defined in the port. In the present invention, such a rigid accessing instrument is laterally deflected away from the implanted catheter by the exterior surface contours of the device. For example, a pair of curved surfaces can be provided on the exterior of the access port which laterally diverge from a leading edge at the device centerline. As a result, any inserted instrument inadvertently missing the entrance orifice of the port in traveling along the exterior surface of the port will engage one of the two curved surfaces and be deflected laterally away from the implanted catheter.

Various accessing approaches are possible using the access ports in accordance with the present invention including conventional needles, sharp trocars, blunt instruments, and catheter-over-needle combinations such as the ANGIO-CATH™. Yet another access instrument combines the skin penetration capabilities of a sharpened metal instrument with the flexibility of an external filament. These devices, also referred to as "self-introducing catheters". While all of the above filaments could be utilized with the present invention, it is believed that its greatest utility will be with a self-introducing catheter or catheter-over-needle variety.

Additional benefits and advantages of the present invention will become apparent to those skilled in the art to which this invention relates from the subsequent description of the preferred embodiments and the appended claims, taken in conjunction with the accompanying drawings.

BRIEF DESCRIPTION OF THE DRAWINGS

FIG. 1 is a perspective view of an access port assembly in accordance with this invention incorporating novel internal features and providing a shielding feature for an internal catheter is provided on the exterior of the access port;

FIG. 2 is a top plan view of a portion of the access port seen in FIG. 1;

FIG. 3 is a cross-sectional view taken along line 3—3 of FIG. 1;

FIG. 3a is an enlarged view taken along line 3a in FIG. 3;

FIG. 4 is an exploded view of an articulating valve assembly as used in at least one embodiment of the present invention;

FIG. 5 is a cross sectional view similar to that of FIG. 3 illustrating a second embodiment of a catheter stop according to the principles of the present invention;

FIG. 5a is an enlarged sectional view of a portion of a catheter stop seen in FIG. 5 and generally encircled by line 5a;

FIG. 6 is a cross sectional view similar to that seen in FIG. 3 illustrating an embodiment of this invention in which normal condition sealing is provided by an elongated self-flattening or self-occluding tube section which is not penetrated by an inserted catheter or filament and implementing an O-ring to provide use condition sealing;

FIG. 7 is a cross sectional view similar to that seen in FIG. 6 illustrating another embodiment of the present invention in which the use condition and normal condition sealing functions of the access port are performed by a separate component in the access port;

FIG. 8 is a cross sectional view substantially similar to that seen in FIGS. 6 and 7 in which a third embodiment of the present is provided where the use and normal condition sealing functions are separated and performed by individual elements of the access device;

DETAILED DESCRIPTION OF THE PREFERRED EMBODIMENT

Figure 3B:
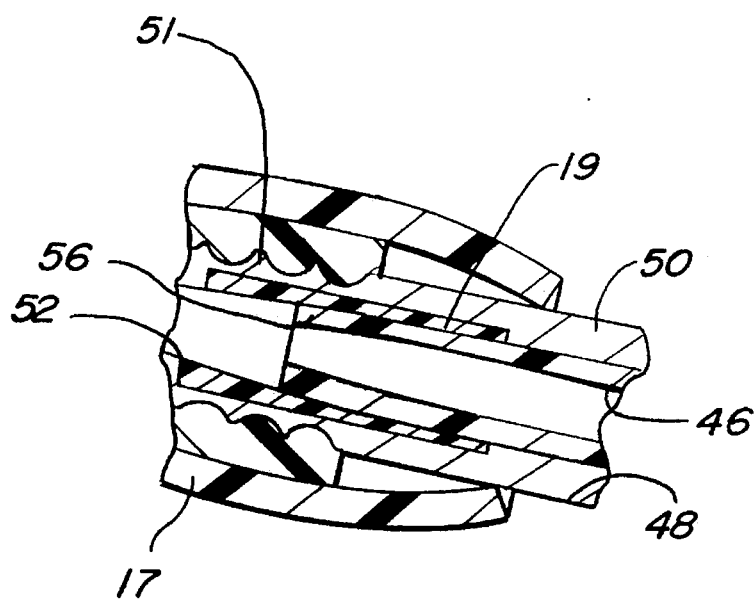
FIG. 3b is a cross-sectional view similar to that of FIG. 3 showing another embodiment of the present invention.

Referring now in detail to the drawings illustrating the various embodiments of the present invention, an access port 10 embodying the principles of the present invention is respectively illustrated in FIG. 1. The access port 10 includes a housing 12 formed from two separate components, a central body 14 and a discharge plug 16. The plug 16 is provided with threads 18 which engage corresponding threads formed in the body 14. These and other features of the access port 10 provide the capability of constructing the access port 10 out of two separate materials. The body 14 can be formed of a hard material which is resistant to penetration and damage by a sharp accessing instrument such as a needle. The plug 16 can be formed from a less hard and cheaper material such as a polymer since it is not directly exposed to or engaged by a sharp accessing instrument. The housing 12 is also provided with a substantially flat base 20 which operates to define a surface which will support the port 10 in a location within the body of the patient. Apertures 22 may be defined in the base to permit securement of the port 10 (by staples, sutures or other means) in a specific location and to a specific tissue within the body of a patient.

Defined in one end of the body 14 is inlet orifice 24 which is defined by a funnel shaped surface 25. The funnel shaped surface 25 and the inlet orifice 24 operate as a target area at which the accessing instrument (not shown) is directed through a percutaneous route.

In the event that the person attempting to access the port 10 completely misses the entrance orifice 24, the accessing instrument may progress along the exterior of the port generally towards the discharge plug 16 and the implanted catheter 17 attached thereto. However, the accessing instrument is prevented from engaging or otherwise contacting the implanted catheter 17 by a pair of deflecting or shielding surfaces 26. These surfaces 26 are curved surfaces which laterally diverge from a leading edge 28 that is generally oriented along a central axis of the housing 12. Upon striking the shielding surfaces 26, the sharp accessing instrument will be deflected away from the central axis of the housing 12 and away from the internal catheter 17. Obviously, different shapes and structures could be utilized to shield the internal catheter 17 from an errant accessing instrument. Of course, such equivalents are deemed to be within the purview of the present invention.

A properly directed accessing instrument is guided by the funnel shape 25 of the entrance orifice 24 into a first or inlet passageway 30 through the housing 12. The inlet passageway 30 defines an inlet axis 31 which is redirected or angularly oriented with respect to a center axis defined through the funnel shaped surface 25 of the entrance orifice 24. This change of direction by the inlet passageway 30 operates as a stop which prevents further insertion of a rigid accessing instrument such as a metal needle through the access port.

The inlet passageway 30 terminates and opens into an enlarged generally cylindrical cavity 32 in which is received an articulating catheter valve assembly 34. In the illustrated embodiments of FIGS. 3–5, the access port 10 of the present invention is provided with a leaflet valve assembly including a pair of resilient disks 36 each of which has at least one slit 38 defined partially across its center. Preferably the slits 38 will be oriented on mutually perpendicular axes with respect to one another. Adhesive 40 may be applied between the disks 36 to maintain a desired rotational indexing of the two disks 36. A doughnut or ring valve 42 having a central aperture 44 is located downstream of the disks 36 and may or may not be adhesively secured thereagainst. As seen in FIG. 3, the leaflet valve assembly 34 is maintained within the cavity 32 by the threading of the plug 16 into engagement with the threads 18 on the central body 14.

Upon detailed inspection of FIG. 3, it will be noticed that the center line or cavity axis 35 through the middle of the leaflet valve assembly 34 and cavity 32 does not coaxially correspond with the inlet axis 31 of the inlet passageway 30. While generally oriented in a common vertical plane, the two axes 31 and 35 are angled relative to one another. The angularity of the cavity axis 35 can be either inclined or declined relative to inlet axis 31. As illustrated, the cavity axis 35 is inclined relative to the inlet axis 31. Additionally, at the end of inlet passageway 30 it can be seen that the cavity axis 35 and valve assembly 34 are vertically offset from the inlet axis 31 and the inlet passageway 30. While shown as being offset vertically downward, depending on the angularity between the two axes 31 and 35 and the distance between the inlet passageway 30 and the outlet passageway, the offset could also be vertically upward. In other words, where the entrance orifice 24 is oriented downwardly (as seen in FIG. 3) and the inlet passageway 30 is angled upward with respect thereto, the cavity 32 and the leaflet valve assembly 34 will be offset vertically downward from the inlet passageway.

This offset is provided so as to accommodate the resiliency of an inserted flexible filament such as a catheter, guide wire, steering wire optical fiber or other device, hereinafter catheter 46. As seen in FIG. 3, after maneuvering the bend of the inlet passageway 30, the resiliency or bias of the catheter 46 is toward the outward side of the bend in the inlet passageway 30. In the illustrated embodiments this bias is away from the skin downward or to the interior of the patient's body. By offsetting the cavity 32 and leaflet valve assembly 34 as described above, the external catheter 46 is caused to engage the center of the leaflet valve assembly 34 thereby minimizing wear and ensuring proper engagement.

Proceeding from the cavity 32, an outlet passageway 48 is defined through the discharge plug 16 and the discharge fitting 50 to which the internal catheter 17 is mounted. The outlet passageway 48 is constructed so that an inserted catheter 46 cannot be completely passed through the outlet passageway 48 to a point where it would extend beyond the terminal end of the fitting 50 and into the implanted catheter 17. This is achieved in one embodiment by convergently tapering the interior diameter of the outlet passageway 48 in a smooth manner in the direction of the terminal end of the fitting 50. This tapering is generally designated at 52 and is such that the outlet passageway 48 circumferentially engages the exterior perimeter of the catheter 46 providing a positive stop which can be felt upon inserting the catheter 46. This tactile feel provides an indication that the device has been properly accessed and the accessing filament placed in a proper docked condition. This feature is particularly useful when physical presence of the inserted catheter within the implanted catheter is not desired.

Alternatively, the taper 52 of the outlet passageway 48 can be formed in a molded elastomeric section 19 which is in turn insert molded into the discharge plug 16. This is seen in FIG. 3b. Such a construction would decrease machining costs and the molded section 19 would itself provide a positive stop for the catheter 46, a perimeter seal for the catheter 46 and would inherently provide a degree of adhesion resisting the inadvertent pulling out of the catheter 46. Further, ribs could be formed on the tapered interior passageway to provide a tactile perception of when full insertion of the catheter 46 occurred.

In the above two embodiments, if the accessing catheter is of the appropriate size, the taper of the passageway will not operate as a stop, but will only provide for a perimeter seal around the accessing catheter while still allowing the catheter to be further inserted. This can be configured so that the perimeter seal is achieved either before or after the accessing catheter reaches the implanted catheter. As such, this feature might prove desirable in a reduced flow or home infusion settings and is further described below.

An alternative embodiment of the positive stop for an external catheter is generally illustrated in FIGS. 5 and 5a where the port 10 is identical to the port 10 illustrated in FIGS. 1–4 except for the specific structure of the positive stop. In this alternative embodiment, the previously mentioned smooth taper 52 in the outlet passageway 48 is replaced with a series of progressively reduced diameter steps 54. The steps 54 operate in the same manner as the taper 52 in that the catheter 46 is introduced and extended through the housing 12 until its terminal end engages the reduced diameter step 54 which closely approximates the exterior diameter of the catheter 46. At that point, the terminal end of the catheter 46 will engage the rise of one of the steps 54. During insertion of the catheter 46, this positive engagement of the catheter 46 with the step 54 will be felt through the catheter 46 by the person inserting the catheter 46 thereby providing a positive indication that the catheter 46 has been properly and fully introduced into the port 10.

As seen in FIGS. 3, 3a, 3b, 5 and 5a, the terminal end of the catheter 46, in this case a catheter, may itself be tapered in a slightly converging manner. This not only allows for easier initial insertion of the catheter 46 into the port 10, but also ensures that a good perimeter seal is made between the exterior surface of the catheter 46 and the surfaces defining the catheter stop in the outlet passageway 48.

While the embodiments of the positive stop illustrated in FIGS. 3 and 5 perform a function of establishing a perimeter seal about the terminal end 56 of the catheter 46 for use condition sealing, the primary function of establishing a perimeter seal about the catheter 46 is performed by the doughnut valve of the leaflet valve assembly. It can be seen that the function of providing normal condition and use condition sealing through the port are provided by a single valve assembly. In FIGS. 6, 7 and 8, three alternative embodiments are provided where the functions of preventing backflow through the port 10 when it is not being used (normal condition sealing) and establishing a perimeter seal about the catheter 46 during infusion (use condition sealing) are performed by two separate structures which are in turn spaced apart from one another along the passageway through the port 10. In two of the embodiments (FIGS. 6 and 8), the fluid pressure of the infused fluid is utilized to open the valving structure which, in the normal condition, prevents backflow through the port 10. In the other embodiment (FIG. 7), the valving structure is engaged by the inserted catheter 46 and opened. Accordingly, the perimeter sealing structure is located downstream of the valving structure in this latter embodiment and upstream of the valving structure in the other two embodiments. Again, as these terms are being used herein, upstream and downstream are to be determined relative to the source for the accessing catheter.

Referring now to FIG. 6, it can be seen that a tube valve 58, the illustrated being a self-flattening occlusive conduit 58, is frictionally engaged over the barbs 51 of the discharge fitting 50. The opposing end of the conduit 58 is secured to the implanted catheter 17 through a conventional attaching method. The occlusive conduit 58 is constructed of a resilient material and in a manner which causes the conduit 58 to flatten and completely occlude when the fluid pressure on the inside of the conduit 58 is less than or equal to the pressure acting on the exterior of the conduit 58. As seen in FIG. 6, the conduit 58 is fully occluded and prevents the backflow of fluid through the internal catheter 17 and into the access port 10. Upstream of the conduit 58, generally at the end of the inlet passageway 30, an O-ring or similar sealing member 60 is located and held within a recessed groove defined in the body 14. The internal diameter of the O-ring 60 is slightly greater than the tapered terminal end 56 of the catheter 46 but is slightly less than the maximum diameter of the catheter 46 at that location when the catheter 46 is fully inserted into the housing 12. In this manner, the O-ring 60 will engage the outer diameter of the catheter 46 and form a perimeter seal about the catheter 46 during the infusion through the port 10 thus providing use condition sealing. The diameter of the O-ring 60 is such that it does not limit or inhibit insertion or withdrawal of the catheter 46.

Figure 9:
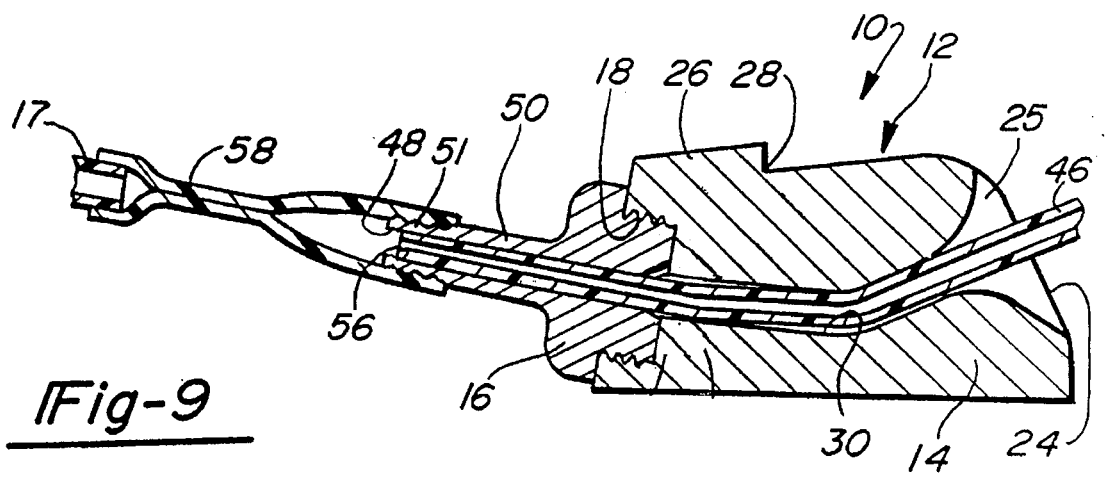
FIG. 9 is a cross-sectional view similar to that seen in FIG. 6 illustrating another embodiment of the present invention showing an elongated self-flattening or self-occluding tube section which has not been penetrated by an inserted catheter.
Figure 10:
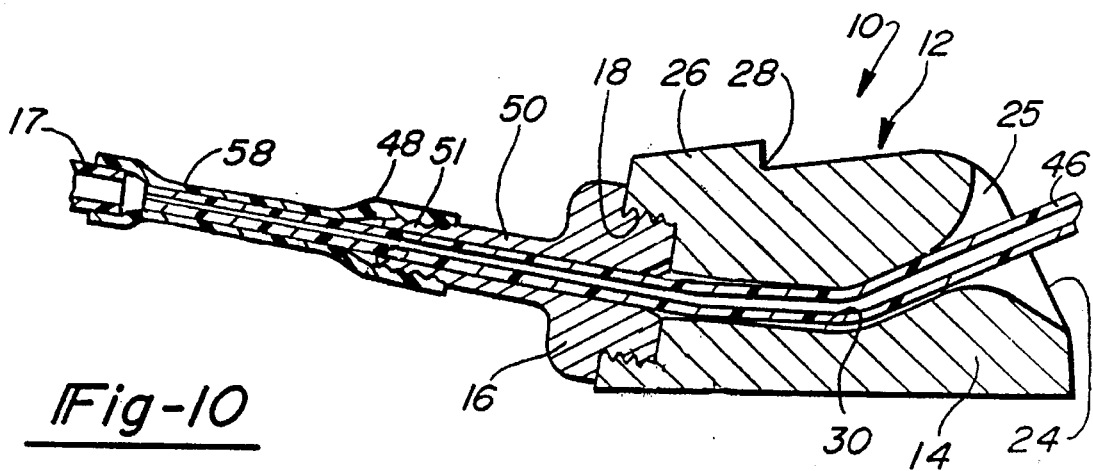
FIG. 10 is a cross-sectional view substantially similar to that seen in FIG. 9 illustrating an elongated self-flattening or self-occluding tube section which has been penetrated by an inserted catheter or filament.

As briefly mentioned above, in some applications, it may be possible to provide use condition sealing strictly through the engagement between the accessing catheter 46 and the conduit 58, eliminating the need for O-ring 60. In such an embodiment, shown in FIGS. 9 and 10, the accessing catheter 46 is provided with a predetermined diameter that allows it to enter into and through the collapsible conduit 58, which may or may not be unitarily formed with the implanted catheter 17. With the diameter of the accessing catheter 46 approximating or being slightly greater than the diameter of the conduit 48 when inflated, a perimeter seal will be formed about the accessing catheter 46 between it and the conduit 48 and an extremely small access port 10 can be constructed.

Alternatively, the tube valve 58 could be embodied as a slit in the tip or side of the catheter 17 itself, the slit being resiliently biased in a closed condition by the natural state or condition of the tube and opening upon an increased pressure within the catheter 17. In a further embodiment, the catheter 17 could be provided with an internal structure, such as a bladder, defining the slit.

Referring now to FIG. 7, it can be seen that the leaflet valve assembly 34 of FIG. 5 has been replaced with a flapper valve assembly 64. The flapper valve assembly 64 operates as a one-way check valve and prevents the backflowing of fluid through the port 10 in the normal condition. Accordingly, the flapper valve assembly 64 is provided with a resilient member or flapper 66 which is deflected out of sealing engagement with the remainder of the flapper valve assembly 64 during insertion of the catheter 46 into the port 10. Downstream of the flapper 66 is an O-ring 68 whose inner diameter is such that it will engage the exterior of the inserted catheter 46 and form a perimeter seal therearound during infusion of medicaments through the port 10. The O-ring 68 is located within the outlet passageway 48 received within a recessed groove 70 and operates in a similar fashion to the O-ring 60 in FIG. 6. Upstream of the flapper 66, the flapper valve assembly 64 includes an elastomeric disk 72 having an aperture 74 which is greater than the outer diameter of the catheter 46. This disk 72 defines the surfaces against which the flapper 66 is sealing engaged when infusion is not being performed.

The final embodiment of the present invention is illustrated in FIG. 8. This embodiment has some similarities to the embodiment of FIG. 6 in that the normal condition backflow preventing function of the access port 10 is performed by a valve assembly located downstream from a separate structure which performs the use condition perimeter sealing function during infusion. The normal condition sealing function is performed in this embodiment by a ball check valve assembly 74.

In this valve assembly 74, a ball 76 is located within a chamber 78 defined within a housing 80. The ball 76 is biased by a spring 82 against the flow of infused fluids and will engage a valve seat 84 generally adjacent to the inlet fitting 86 of the housing 80. The inlet fitting 86 is attached by a conduit connector 88 extended therebetween to the barbs 51 of the discharge fitting 50. The outlet fitting 90 of the check valve assembly 74 is threadably received into one end of the housing 80 to enable changing and repair of the ball 76 and spring 82 if and when needed. The opposing end of the outlet fitting 90 is connected to the internal catheter 17 in a conventional and well known manner.

In the same manner as described above in connection with FIG. 6, an O-ring 60 is located within a recessed groove 62 defined in the body 14 of the housing 12 and generally adjacent to the end of the outlet passageway 48. This O-ring 60 is similarly provided with an inner diameter that is slightly less than the exterior diameter of the catheter 46 at that location when the catheter 46 is fully inserted into the port 10. Medicaments being infused through the catheter 46 provide a positive fluid pressure which is sufficient to overcome the biasing force of the spring 82 and therefore causes the ball 76 to unseat from the valve seat 84 allowing the infused fluids to be provided to the internal catheter 70 and the desired treatment sight. The O-ring 60 accordingly forms a perimeter seal about the catheter 46 during infusion.

In addition to the above described style of check valve, the valve assembly 74 could utilize a construction in which a ball is capable of being biased either upstream or downstream of a closed, center neutral position where flow through the valve 74 is obstructed. Such a valve assembly 74 would permit both infusion and withdrawal of fluids from the patient, depending on the pressure differential applied to the valve assembly 74.

While the above description constitutes the preferred embodiment of the present invention, it will be appreciated that the invention is susceptible to modification, variation and change without departing from the proper scope and fair meaning of the accompanying claims.

We claim:

1. An implantable access device which permits the introduction of an external filament such as a catheter, guide wire or optical fiber into a patient for communication with an internal catheter located within the body of the patient, said device comprising:

a housing having portions defining an inlet opening, an outlet opening, a passageway communicating between said inlet and outlet openings, said passageway including an inlet portion and an outlet portion, said inlet opening being generally funnel shaped and guiding an external filament inserted percutaneously into said inlet portion of said passageway, said outlet portion of said passageway terminating in said outlet opening and said outlet opening being defined in a nipple adapted for having the internal catheter attached thereto;

first sealing means for providing resistance to the flow of fluid through said passageway when said external filament is not present within said device yet allowing the transfer of fluids through said passageway when said filament is present within said passageway; and second sealing means for engaging and sealing about the exterior perimeter of an external filament when inserted into said device.

2. An implantable device as set forth in claim 1 wherein said second sealing means is separate and distinct from said first sealing means.

3. An implantable access device as set forth in claim 1 wherein said second sealing means is a O-ring.

4. An implantable access device as set forth in claim 1 wherein said second sealing means is a donut valve.

5. An implantable access device as set forth in claim 1 wherein said second sealing means is located downstream of said first sealing means.

6. An implantable access device as set forth in claim 1 wherein said second sealing means is located upstream of said first sealing means.

7. An implantable access device as set forth in claim 1 wherein said first sealing means comprises a leaflet valve.

8. An implantable access device as set forth in claim 1 wherein said first sealing means comprises a flapper valve.

9. An implantable access device as set forth in claim 1 wherein said first sealing means comprises a fluid actuated check valve.

10. An implantable access device as set forth in claim 8 wherein said check valve is a ball check valve.

11. An implantable access device as set forth in claim 8 wherein said ball check valve is a spring biased ball check valve.

12. An implantable access device as set forth in claim 1 wherein said first sealing means includes a collapsible conduit, said collapsible conduit collapsing and being substantially occluded when pressure within said conduit is less than or equal to pressure acting on the exterior of said conduit.

13. An implantable access device as set forth in claim 12 wherein said collapsible conduit is attached to said nipple and adapted for attachment to the internal catheter.

14. An implantable access device as set forth in claim 12 wherein said second sealing means comprises engagement between an external filament and said collapsible conduit, the external filament being receivable within said collapsible conduit.

15. An implantable access device as set forth in claim 1 wherein said second sealing means comprises engagement between an external filament and features formed by said housing passageway.

16. An implantable access device as set forth in claim 1 wherein said first sealing means is separate and distinct from said housing.

17. An implantable access device as set forth in claim 1 wherein said second sealing means is defined by a convergently tapered portion of said passageway.

18. An implantable access device as set forth in claim 17 wherein said tapered portion tapers to a diameter preventing passage of the filament therethrough.

* * * * *